United States Patent [19]

Billah

[11] Patent Number: 5,334,592
[45] Date of Patent: Aug. 2, 1994

[54] CERTAIN PAF ANTAGONIST ANTIHISTAMINE COMBINATIONS AND METHODS

[75] Inventor: M. Motasim Billah, Edison, N.J.

[73] Assignee: Schering Corporation, Kenilworth, N.J.

[21] Appl. No.: 960,229

[22] Filed: Oct. 13, 1992

Related U.S. Application Data

[63] Continuation of Ser. No. 582,959, filed as PCT/US89/01671, Apr. 24, 1989, which is a continuation-in-part of Ser. No. 186,535, Apr. 27, 1988, abandoned.

[51] Int. Cl.$^5$ ............... A61K 31/55; A61K 31/50; A61K 31/41; A61K 31/34
[52] U.S. Cl. .................. 514/220; 514/253; 514/357; 514/461; 514/826
[58] Field of Search ............ 514/220, 557, 253, 357, 514/461, 826

[56] References Cited

U.S. PATENT DOCUMENTS

| | | | |
|---|---|---|---|
| 3,980,790 | 9/1976 | Hester, Jr. | 424/269 |
| 3,987,052 | 10/1976 | Hester, Jr. | 260/308 R |
| 4,350,695 | 9/1982 | Westwood et al. | 514/826 X |
| 4,539,332 | 9/1985 | Biftu et al. | 514/461 |
| 4,595,693 | 6/1987 | Biftu et al. | 514/461 |
| 4,621,094 | 11/1986 | Findlay et al. | 514/357 |

FOREIGN PATENT DOCUMENTS

| | | |
|---|---|---|
| 154887 | 9/1985 | European Pat. Off. . |
| 3502392 | 7/1986 | Fed. Rep. of Germany . |

OTHER PUBLICATIONS

Science vol. 226, Platelet–Activating Factor–Induced of Human Platelets Specifically Inhibited by Trizolobenzodiazepines Sep. 28, 1984, pp. 1454–1455.
Touvay et al. Oral effects of BN1267, A novel Peripheral Antihistamic compound on Antigen-OR PAF--Acether ... (1986) p. 194 (6th International Conf.).
Piwinski et al. Chap. 8 Pulmonary & Antiallergy Agents (1978).

*Primary Examiner*—Marianne M. Cintins
*Assistant Examiner*—K. Weddington
*Attorney, Agent, or Firm*—Henry C. Jeanette; Matthew Boxer

[57] ABSTRACT

Methods and compositions are disclosed employing combinations of antihistamines with certain diaryl tetrahydrofuran, diaryl tetrahydrothiophene, triazolobenzodiazepine or thienotriazolodiazepine PAF-antagonist compounds in the treatment of allergic reactions.

9 Claims, No Drawings

CERTAIN PAF ANTAGONIST ANTIHISTAMINE COMBINATIONS AND METHODS

This application is a continuation of U.S. application Ser. No. 07/582,959 filed on Oct. 11, 1990, now abandoned which in turn is the United States National Application corresponding to International Application No. PCT/US 89/01671, filed Apr. 24, 1989 and designating the United States, which PCT Application is in turn a continuation-in-part of U.S. application Ser. No. 186,535, filed Apr. 27, 1988, now abandoned the benefit of which applications is claimed pursuant to the provisions of 35 U.S.C. §§ 120, 363 and 365(C).

BACKGROUND OF THE INVENTION

The present invention relates to combinations of certain diaryl tetrahydrofuran, diaryl tetrahydrothiophene, triazolobenzodiazepine or thienotriazolodiazepine derivatives with antihistamines and the use thereof to treat allergic reactions.

Several mediators possessing a broad spectrum of potent biological activities are released during allergic reactions. Prominent among these mediators are histamine, leukotrienes and platelet-activating factor (PAF).

Compounds which prevent the effects of the mediators are thus of interest in treating allergic reactions. For example, numerous antihistamines are known in the art. Chlorpheniramine, brompheniramine, clemastine, ketotifen, azatadine, loratadine, and terfenadine are examples of commercially available or soon to be available antihistamines.

Various compounds have been disclosed as PAF antagonists. For example, compounds of the formula Ia or Ib

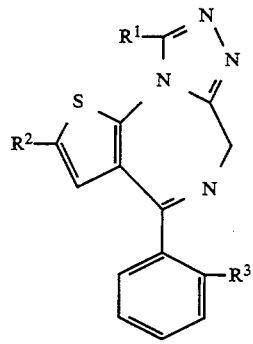

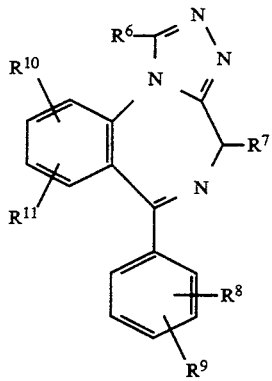

(wherein $R^1$, $R^2$, $R^3$, $R^6$, $R^7$, $R^8$, $R^9$, $R^{10}$ and $R^{11}$ are as defined below) are disclosed as PAF antagonists in *Science*, Vol. 226, p. 1454 (1984) and German Offenlegungsschrift 35 02 392 A1.

Compounds of the formula II

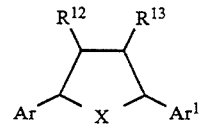

(wherein $R^{12}$ $R^{13}$, Ar, $Ar^1$ and X are as defined below) are also disclosed as PAF antagonists in Biftu et al., U.S. Pat. Nos. 4,539,332 and 4,595,693 and European Patent Application No. 0 154 887 A1.

Antihistamines have proven useful in the treatment of certain allergic disorders such as seasonal rhinitis. However, the antihistamine therapy is ineffective in such complex allergic disorders as asthma indicating that histamine is only one of several mediators released during an allergic response. Indeed, in guinea pigs, allergic bronchospasm appears to be composed of three distinct components, mediated separately be histamine, leukotrienes and PAF.

PAF shares with histamine the abilities to cause bronchospasm and vasopermeability. In addition, PAF induces non-specific bronchial hyperreactivity in man as well as in animals.

Touvay et al., 6th International Conference on Prostaglandins, Florence, Italy, Jun. 3–6, 1986, p. 914, disclose BN1267 and related compounds of the general formula

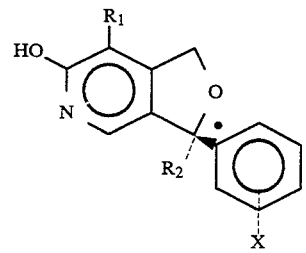

which compounds are said to exhibit antihistaminic activity. The presentation also mentions that ". . . the association of this dose [10 mg/kg p.o.] of BN 1267 with a non-active dose of a specific PAF-receptor antagonist BN 52021 ($-10\%$ at 2 mg/kg p.o.) administered one hour before PAF-acether significantly antagonized the bronchospasm ($-45\%$ p $<0.01$)." BN 52021 is ginkgolide B having the structure:

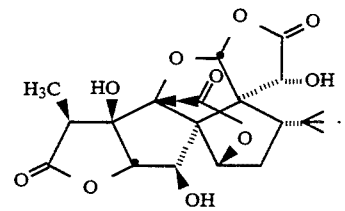

While we have found that representative examples of the above PAF antagonists prevent PAF-induced lethality, we have also found that they do not provide protection against allergic death (anaphylactic shock) in sensitized mammals, such as ovalbumin sensitized mice. Antihistamines such as chlorpheniramine, clemastine and ketotifen provided only partial protection against ovalbumin-induced lethality.

SUMMARY OF THE INVENTION

It has now surprisingly been found that complete or at least potentiated protection against allergic reactions such as antigen-induced death in mammals can be achieved by administering to such mammal an antiallergic effective amount of a combination comprising
(1) a PAF-antagonist
(a) of the formula Ia or Ib

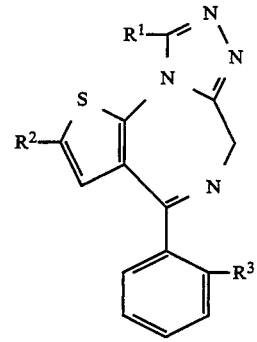

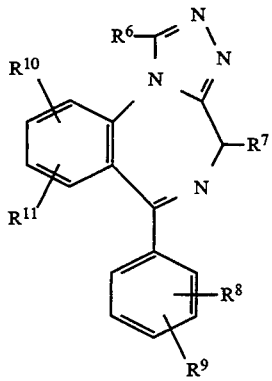

or a pharmaceutically acceptable salt or solvate of a compound Ia or Ib, wherein:

$R^1$ is H, lower alkyl of 1 to 4 carbon atoms, cyclopropyl, methoxy, chloro or bromo,
$R^2$ represents

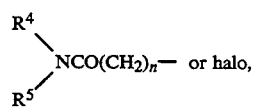

$R^3$ represents H, chloro or bromo,
$R^4$ and $R^5$ may be the same or different and each is independently selected from H, alkyl of 1 to 4 carbon atoms or hydroxyalkyl having from 1 to 4 carbon atoms, or $R^4$ and $R^5$ together with the nitrogen atom attached thereto represent a 5, 6 or 7 membered, saturated ring, which ring optionally contains another heteroatom or hereto group selected from —O—, —S—, —NH— or —N(CH$_3$)—,
n represents 0, 1, 2, 3, 4, 5, 6, 7 or 8,
$R^6$ represents H, lower alkyl of 1 to 3 carbon atoms, phenyl, benzyl or COOR',
$R^7$ represents H or alkyl of 1 to 3 carbon atoms,
$R^8$, $R^9$, $R^{10}$ and $R^{11}$ may be the same or different and each independently represents H, alkyl of 1 to 3 carbon atoms, halo, nitro, cyano, trifluoromethyl, alkoxy, alkylthio, alkylsulfinyl, alkylsulfonyl, alkanoylamino or dialkylamino, wherein each alkyl portion of alkoxy, alkylthio, alkylsulfinyl, alkylsulfonyl, alkanoylamine or dialkylamino contains 1 to 3 carbon atoms, R' represents alkyl of 1 to 4 carbon atoms; or
(b) of formula II

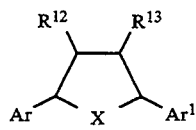

wherein:

X is O, S, SO, or SO$_2$,
$R^{12}$ and $R^{13}$ may be the same or different and each independently represents H, lower alkyl of 1 to 6 carbon atoms, halo, halo-lower alkyl of 1 to 6 carbon atoms CONR$^{14}$R$^{15}$ lower alkenyl of 1 to 6 carbon atoms lower alkynyl of 1 to 6 carbon atoms, COR$^{14}$, COOR$^{14}$, CH$_2$OR$^{14}$, CH$_2$NR$^{14}$R$^{15}$, CH$_2$SR$^{14}$, =O or OR$^{15}$, Ar and Ar$^1$ may be the same or different and each independently represents pyrryl, furyl, pyridyl, thienyl, cyclohexyl, naphthyl or a group of the formula

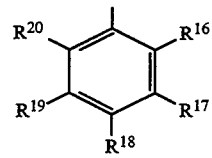

$R^{14}$ and $R^{15}$ may be the same or different and each is independently H or lower alkyl of 1 to 6 carbon atoms;

$R^{16}$, $R^{17}$, $R^{18}$, $R^{19}$ and $R^{20}$ may be the same or different and each is independently H, —OR$^{14}$, —SR$^{14}$, —SOR$^{14}$, —SO$_2$R$^{14}$, —OCF$_3$, —SCF$_3$, —NR$^{14}$R$^{15}$, —OCH$_2$CO$_2$R$^{14}$, —SO$_2$NR$^{14}$R$^{15}$, —CO$_2$R$^{14}$, —N(R$^{14}$)SO$_2$R$^{15}$, COR$^{14}$, NO$_2$ or CN, or R$^{16}$ and R$^{17}$, R$^{17}$ and R$^{18}$, R$^{18}$ and R$^{19}$ or R$^{19}$ and R$^{20}$ together represent a —OCH$_2$O—, —OCH$_2$CH$_2$O— or —OCH$_2$CH$_2$NR$^{14}$— bridge; and (2) an antihistamine, which is preferably selected from chlorpheniramine, brompheniramine, clemastine, ketotifen, azatadine, loratadine, terrenadine, cetirizine, astemizole, tazifylline, levocabastine, diphenhydramine, temelastine, etolotifen, acrivastine, azelastine, ebastine, mequitazine, and the compounds 3-amino-9,13b-dihydro-1H-dibenz[c,f]imidazo[1,5-a]azepine[WAL-801CL], 1-(2-ethoxyethyl)-2-(4-methyl-1-homopiperazinyl)-benzimidazole[KB-2413], 2-(dimethylamino)ethyl-2,3-dihydro-4-methylpyrido[3,2-f]-1,4-oxazepine-5(4H)-thione[AHR 11325], or a pharmaceutical acceptable salt of such compounds.

The present invention also contemplates a pharmaceutical composition comprising such combination together with a pharmaceutically acceptable carrier and a method for making said composition.

Also included in the present invention is the use of a PAF antagonist of formula Ia, Ib or II (above) in combination with an antihistamine for the manufacture of a medicament for treating allergy.

In the compounds of formula Ia, $R^1$ is preferably $CH_3$ and $R^3$ is preferably chloro or bromo. $R^2$ is preferably Br or $R^4R^5NCO(CH_2)_n$. $R^4$ and $R^5$ are preferably selected from H, methyl, ethyl or hydroxyethyl or $R^4$ and $R^5$ together represent morpholino, and n is preferably 2.

In one embodiment of the method or composition of the invention, the compound of formula Ia or Ib is selected from 8-chloro-1-methyl-6-phenyl-4H-s-triazolo[4,3-a][1,4]benzodiazepine,
8-chloro-1-methyl-6-(o-fluorophenyl)-4H-s-triazolo[4,3-a][1,4]benzodiazepine,
1-methyl-6-phenyl-4H-s-triazolo[4,3-a][1,4]benzodiazepine,
8-chloro-1-propyl-6-phenyl-4H-s-triazolo[4,3-a][1,4]benzodiazepine,
8-chloro-1-isopropyl-6-phenyl-4H-s-triazolo[4,3-a][1,4]benzodiazepine,
8-chloro-1-ethyl-6-phenyl-4H-s-triazolo[4,3-a]-[1,4]benzodiazepine,
1-methyl-6-phenyl-8-(trifluoromethyl)-4H-s-triazolo[4,3-a][1,4]benzodiazepine,
8-chloro-1-methyl-6-(o-chlorophenyl)-4H-s-triazolo[4,3-a][1,4]benzodiazepine,
4-(2-chlorophenyl)-9-methyl-6H-thieno[3,2-f]-[1,2,4]triazolo[4,3-a][1,4]diazepine-2-propionic acid morpholide,
4-(2-chlorophenyl)-9-methyl-6H-thieno[3,2-f]-[1,2,4]triazolo[4,3-a][1,4]diazepine-2-propionamide,
4-(2-chlorophenyl)-9-cyclopropyl-6H-thieno-[3,2-f][1,2,4]triazolo[4,3-a][1,4]diazepine-2-propionic acid morpholide, or
4-(2-chlorophenyl)-9-methyl-6H-thieno[3,2-f]-[1,2,4]triazolo[4,3-a][1,4]diazepine-2-propionic acid diethyl amide.

Preferably, the compound of formula Ia or Ib is
4-(2-chlorophenyl)-9-methyl-6H-thieno[3,2-f]-[1,2,4]triazolo[4,3-a][1,4]diazepine-2-propionic acid morpholide (WEB 2086),
8-chloro-6-(2-chlorophenyl)-1-methyl-4H-s-triazolo[4,3-a][1,4]benzodiazepine (triazolam), or
8-chloro-1-methyl-6-phenyl-4H-3-triazolo-[4,3-a][1,2]-benzodiazepine (alprazolam).

In another embodiment of the composition of the invention, the PAF antagonist is of the formula IIa, IIb or IIc:

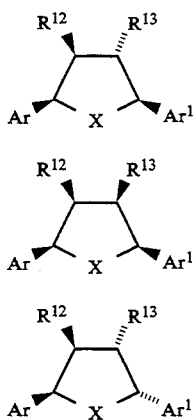

wherein X, $R^{12}$ $R^{13}$ Ar and $Ar^1$ are as defined above. Preferably, Ar and $Ar^1$ independently represent. 2,4-dimethoxyphenyl or 3,4,5-dimethoxyphenyl. X is preferably O or S, more preferably S. $R^{12}$ and $R^{13}$ preferably independently represent H or $CH_3$.

Suitable compounds of formula II for use in the present method and composition include
2,5-bis(3,4-dimethoxyphenyl)tetrahydrofuran,
2,5-bis(3,4,5-trimethoxyphenyl)tetrahydrofuran,
2,5-bis(3,4,5-trimethoxyphenyl)tetrahydrothiophene, and
2-(3-methoxy-5-methylsulfonyl-4-propoxyphenyl)-(3,4,5-trimethoxyphenyl)tetrahydrofuran, preferably in their respective trans forms. 3,4-Dimethylated forms of such compounds are also contemplated. One preferred compound is trans-2,5-bis(3,4,5-trimethoxyphenyl)tetrahydrofuran (L-652,731).

The antihistamine employed in the method and composition of the invention is preferably selected from chlorpheniramine, ketotifen, loratadine, terrenadine, clemastine or astemizole.

DETAILED DESCRIPTION OF THE INVENTION

The compounds of formula Ia and Ib are known, e.g. from German Offenlegungsschrift No. 35 02 392 A1 and U.S. Pat. Nos. 3,987,052, and 3,980,790 as are the methods for preparing such compounds.

The compounds of formula II and the methods for preparing such compounds are also known, e.g., from U.S. Pat. Nos. 4,595,693 and 4,539,322 and in European Patent Application No. 0 154 887 A1.

Any antihistamine can be employed in the present invention. Suitable antihistamines include chlorpheniramine, bromopheniramine, clemastine, ketotifen, azatadine, loratadine, terfenadine, cetirizine, astemizole, tazifylline, levocabastine, diphenhydramine, temelastine, etolatifen, acrivastine, azelastine, ebastine, mequitazine, and the compounds
3-amino-9,13b-dihydro-1H-dibenz[c,f]imidazo[1,5-a]azepine[WAL-801CL],
1-(2-ethoxyethyl)-2-(4-methyl-1-homopiperazinyl)-benzimidazole[KB-2413],
2-(dimethylamino)ethyl-2,3-dihydro-4-methylpyrido-[3,2-f]-1,4-oxazepine-5(4H)-thione[AHR 11325], or a pharmaceutical acceptable salt of such compounds.

The compositions and methods of the invention can be used to treat allergic disorders such as seasonal thiniris, perennial vasomotor thiniris, acute utricaria, chronic utricaria, atopic dermatitis, contact dermatitis, itching pruritides, angloedema, conjunctivitis, chronic bronchitis, systemic anaphylaxis, serum sickness, and bronchial asthma.

One of the characteristic features of asthma that also occurs in some patients with chronic bronchitis and allergic thiniris is extreme sensitivity of the airways (airway hyperreactivity) to physical, chemical and pharmacological agents. These patients develop a greater degree of bronchospasm to a wider variety of stimuli than do healthy subjects. PAF causes not only acute bronchospasm but also non-specific, sustained airway hyperreactivity in man. Lung inflammation is believed to be central to the establishment of airway hyperreactivity. PAF is a potent mediator of inflammation and histamine, by virtue of its ability to cause vasopermeability, may exacerbate the inflammatory process initiated by PAF. Thus, PAF, either alone or in combination with histamine, might play a critical role in the pathogenesis of asthma and related disorders. Apparently, from our findings inhibition of PAF could not only enhance the efficacy of antihistamine therapy, but also offer additional, new utilities for antihistamines. For instance, the combined use of anti-PAF and antihistaminic agents may be useful in correcting the underlying cause of asthma.

The anti-allergic effect of the combinations of PAF antagonists and antihistamines of the present invention may be demonstrated by the test procedures described below:

PAF-INDUCED LETHALITY IN MICE AND EVALUATION OF IN VIVO ANTI-PAF ACTIVITY OF VARIOUS PHARMACOLOGICAL AGENTS

Swiss-Webster female CFW mice (from Charles River), 5–10 per group, were injected through the tail vein with PAF in 0.5 ml of saline containing bovine serum albumin, and death was recorded. PAF at doses of 100 µg/kg, 150 µg/kg and 200 µg/kg causes 0, 60% and 100% lethality, respectively, and death occurred within 30 minutes. L-652,731 (A), WEB 2086 (B), chlorpheniramine (C) and ketotifen (D) suspended 0.4% methylcellulose vehicle were given intraperitoneally (0.5 ml) 30 minutes before PAF injection. Death occurring within 1 hour after PAF challenge was recorded and the results are shown in Table I below as % lethality.

TABLE I

EFFECTS OF VARIOUS ANTAGONISTS ON PAF-INDUCED LETHALITY IN MICE

| Compound[a] | Dose (mg/kg) | Number of animals | % Lethality | $ED_{50}$ (mg/kg) |
| --- | --- | --- | --- | --- |
| none | — | 38 | 95 | — |
| A | 5 | 6 | 84 | |
|  | 10 | 18 | 72 | 20 |
|  | 25 | 12 | 25 | |
|  | 50 | 18 | 16 | |
| B | 1 | 6 | 84 | |
|  | 2 | 5 | 20 | 1.5 |
|  | 5 | 6 | 16 | |
|  | 10 | 6 | 0 | |
| C | 10 | 6 | 100 | — |
| D | 1.4 | 8 | 100 | — |

[a]Compounds given i.p. 30 minutes before i.v. challenge with PAF (200 µg/kg). Death was recorded 1 hour after the challenge.

SENSITIZATION OF MICE AND INDUCTION OF ANAPHYLACTIC DEATH

Swiss-Weber female CFW mice (20–30 g) from Charles River were acclimatized for 7–14 days. Animals were sensitized by injecting intraperitoneally 0.5 ml of saline containing 1.6 mg of ovalbumin adsorbed to 100 mg of $Al(OH)_3$ gel. Ten to 15 days after sensitization, the animals, at least six per group, were injected intraveneously through the tail vein with 1.6 mg of ovalbumin in 0.5 ml of saline. One hundred percent of the sensitized animals died within 10–20 minutes. Injection of ovalbumin into normal mice caused no lethality. Compounds L-652,731 (A), WEB 2086 (B), chlorpheniramine (C), ketotifen (D) and clemastine (E), and combinations A+C, B+C, A+D, B+D, A+E amd B+E were suspended in 0.4% methylcellulose vehicle. The compositions (given in dosages listed in the left-hand column of Table II below) were administered intraperitoneally either individually or in indicated combinations 30 minutes before challenge with albumin to sensitized mice. Death was recorded 1 hour after the challenge. The results are listed in Table II below.

TABLE II

SYNERGISTIC PROTECTION OF ANAPHYLACTIC DEATH IN SENSITIZED MICE BY COMBINATIONS OF THE INVENTION

| Treatment | Number of Animals[a] | % Survival[a] |
| --- | --- | --- |
| Saline | 38 | 5 |
| A (50 mg/kg) | 16 | 0 |
| B (5 mg/kg) | 11 | 0 |
| C (3 mg/kg) | 24 | 16 |
| A (50 mg/kg) + C (3 mg/kg) | 19 | 84 |
| B (5 mg/kg) + C (3 mg/kg) | 8 | 100 |
| E (0.2 mg/kg) | 18 | 45 |
| A (50 mg/kg) + E (0.2 mg/kg) | 10 | 100 |
| B (5 mg/kg) + E (0.2 mg/kg) | 8 | 100 |
| D (0.1 mg/kg) | 14 | 40 |
| A (50 mg/kg) + D (0.1 mg/kg) | 6 | 100 |
| B (5 mg/kg) + D (0.1 mg/kg) | 8 | 90 |

[a]Pooled data from five separate experiments.

The above results demonstrate that intraveneous administration of PAF (200 µg/kg) induced 100% lethality in mice. PAF antagonists A and B, given intraperitoneally, provided protection against PAF-induced lethality with $ED_{50}$ values of 20 mg/kg and 1.5 mg/kg, respectively (Table I). Neither chlorpheniramine, clemastine nor ketotifen affected PAF-induced mortality (Table I).

When sensitized animals were challenged intraveneously with ovalbumin, nearly 100% of the animals died within 10–20 minutes. The anti-PAF agents A and B, given intraperitoneally at doses as high as 50 mg/kg and 20 mg/kg, respectively, were totally ineffective in protecting these animals from death (Table II). The antihistamines chlorpheniramine, clemastine and ketotifen, given individually, provided significant protection (Table II). This protection varied between 30% and 70% depending on the compound, dose and the batch of animals.

When PAF antagonist A at a ineffective dose, was coadministered with a partially effective dose of either chlorpheniramine, clemastine or ketotifen, the sensitized animals were completely protected from antigen-induced death (Table II). Similar synergistic protection was observed when an ineffective dose of PAF antagonist B was combined with partially effective doses of the individual antihistamines (Table II).

The compositions of the present invention may be administered employing the PAF antagonist together with or separate from the antihistamine. Preferably, a single dosage form is employed. The dosage of the antihistamine is preferably from about 35% to about 100% of the antihistamine's normal or effective dose ($ED_{50}$), more preferably from about 50% to about 100% of the antihistamine's effective dose. The PAF antagonist is preferably administered in amount of from 35% to 200% of its PAF antagonist effective dose ($ED_{50}$) and more preferably from about 50% to about 150% of the effective dose. For example, compound B above has an $ED_{50}$ (p.o.) in guinea pigs (PAF-induced bronchospasm) of 0.1 mg/kg. Similarly compound A above and alprazolam have $ED_{50}$'s (i.v.) in guinea pigs of 0.4 mg/kg and 3 mg/kg, respectively.

The compositions may be administered orally, i.v., etc., and in general by any of the modes by which the individual components may be administered. Of course, the dose will be regulated according to the potency of individual compounds employed, the mode of administration, and the judgment of the attending clinician depending on factors such as the degree and the severity of the disease state and age and general condition of the patient being treated.

The compositions of the invention can be administered in unit dosage forms such as tablets, capsules, pills, powders, granules, sterile parenteral solutions or suspensions, suppositories, transdermal compositions and the like. Such dosage forms are prepared according to standard techniques well known in the art.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for treating allergic reactions in a mammal comprising administering an anti-allergic effective amount of a combination comprising a PAF-antagonist and an antihistamine, said PAF-antagonist being selected from 4-(2-chlorophenyl)-9-methyl-6H-thieno [3,2-f][1,2,4]triazolo [4,3-a][1,4]diazepine-2-propionic acid morpholide and 2,5-bis(3,4,5-trimethoxyphenyl)-tetrahydrofuran, and said antihistamine being selected from chlorpheniramine, clemastine, and ketotifen.

2. The method according to claim 1 characterized in that the PAF-antagonist is 4-(2-chlorophenyl)-9-methyl-6H-thieno[3,2-f][1,2,4]-triazolo [4,3-a][1,4]diazepine-2-propionic acid morpholide and the antihistamine is chlorpheniramine.

3. The method according to claim 1 characterized in that the PAF-antagonist is 2,5-bis(3,4,5-trimethoxyphenyl)tetrahydrofuran and the antihistamine is chlorpheniramine.

4. The method according to claim 1 characterized in that the PAF-antagonist is 4-(2-chlorophenyl)-9-methyl-6H-thieno[3,2-f][1,2,4]-triazolo[4,3-a][1,4] diazepine-2-propionic acid morpholide and the antihistamine is ketotifen.

5. The method according to claim 1 characterized in that the PAF-antagonist is 2,5-bis(3,4,5-trimethoxyphenyl)tetrahydrofuran and the antihistamine is ketotifen.

6. The method according to claim 1 characterized in that the PAF-antagonist is 4-(2-chlorophenyl)-9-methyl-6H-thieno [3,2-f][1,2,4]-triazolo [4,3-a][1,4]diazepine-2-propionic acid morpholide and the antihistamine is clemastine.

7. The method according to claim 1 characterized in that the PAF-antagonist is 2,5-bis(3,4,5-trimethoxyphenyl)tetrahydrofuran and the antihistamine is clemastine.

8. A pharmaceutical composition suitable for treating allergic reactions comprising an anti-allergic effective amount of a PAF-antagonist in combination with an antihistamine, said PAF-antagonist selected from 4-(2-chlorophenyl)-9-methyl-6H-thieno [3,2-f][1,2,4]triazolo [4,3-a][1,4]diazepiine-2-propionic acid morpholide and 2,5-bis(3,4,5-trimethoxyphenyl) tetrahydrofuran, and said antihistamine is selected from chlorpheniramine, clemastine; and ketotifen.

9. A pharmaceutical composition according to claim 8 suitable for treating allergic reactions comprising an anti-allergic effective amount of a of a PAF-antagonist in combination with an antihistamine, said combination selected from (a)  4-(2-chlorophenyl)-9-methyl-6H-thieno[3,2-f][1,2,4]-triazolo [4,3-a][1,4]diazepine-2-propionic acid morpholide and chlorpheniramine, (b)  4-(2-chlorophenyl)-9-methyl-6H-thieno[3,2-f][1,2,4]-triazolo [4,3-a][1,4]diazepine-2-propionic acid morpholide and clemastine, (c)  4-(2-chlorophenyl)-9-methyl-6H-thieno[3,2-f][1,2,4]-triazolo [4,3-a][1,4]diazepine-2-propionic acid morpholide and ketotifen, (d)  2,5-bis(3,4,5-trimethoxyphenyl)tetrahydrofuran and chlorpheniramine, (e)  2,5-bis(3,4,5-trimethoxyphenyl)tetrahydrofuran and clemastine, and (f)  2,5-bis(3,4,5-trimethoxyphenyl)tetrahydrofuran and ketotifen.

* * * * *